US010849877B2

(12) United States Patent
Stroh et al.

(10) Patent No.: US 10,849,877 B2
(45) Date of Patent: Dec. 1, 2020

(54) REDUCTION OF EPILEPTIC SEIZURES

(71) Applicant: EPIPLEX LTD, London (GB)

(72) Inventors: Plamena Rumyanova Stroh, London (GB); Dmitri Tsvetkov, London (GB)

(73) Assignee: EPIPLEX LTD, London (GB)

( * ) Notice: Subject to any disclaimer, the term of this patent is extended or adjusted under 35 U.S.C. 154(b) by 0 days.

(21) Appl. No.: 14/907,038

(22) PCT Filed: Jul. 18, 2014

(86) PCT No.: PCT/GB2014/052205
§ 371 (c)(1),
(2) Date: Jan. 22, 2016

(87) PCT Pub. No.: WO2015/011451
PCT Pub. Date: Jan. 29, 2015

(65) Prior Publication Data
US 2016/0158195 A1 Jun. 9, 2016

(30) Foreign Application Priority Data

Jul. 22, 2013 (GB) .................................. 1313052.1

(51) Int. Cl.
*A61K 31/375* (2006.01)
*A61K 31/194* (2006.01)

(52) U.S. Cl.
CPC .......... *A61K 31/375* (2013.01); *A61K 31/194* (2013.01)

(58) Field of Classification Search
None
See application file for complete search history.

(56) References Cited

FOREIGN PATENT DOCUMENTS

| KR | 100836186 B1 | 6/2008 |
|---|---|---|
| WO | 2011/148203 | 12/2011 |
| WO | 2013/188509 | 12/2013 |

OTHER PUBLICATIONS

Cho et al. In Journal of Neuroscience Research 84(7), 1505-1511 (2006).*
Carvalho et al. In Neurochemistry International 58, 385-390 (2011).*
Santos et al. In Pharmacology, Biochemistry and Behavior 80, 1-5 (2008).*
Yamamoto, H. In Experimental Biology Annual Meeting, New Orleans, LA, USA; Apr. 18-22, 2009.*
Nebendahl, K. In Routes of Administration (2000) at www.usp.br/bioterio/Artigos/Procedimentos%20experimentais/Administration_The_Laboratory_Rat-By_George_J_Krinke-2.pdf (retieved from the internet Jul. 6, 2017).*
Carvalho, A.S.R. et al., "Neuroprotective effect of pyruvate and oxaloacetate during pilocarpine induced status epilepticus in rats," (2011) Neurochemistry International 58:385-390.
Gonzalez-Ramirez, M. et al., "Anticonvulsive effect of vitamin C on pentylenetetrazol-induced seizures in immature rats," (2010) Pharmacology, Biochemistry and Behavior 97:267-272.
Han, P. et al., "Pharmaceutical composition for preventing and treating epliptic seizure, comprises ethyl pyruvate as effective ingredient," WPI Abstract Accession No. 2009-B40221.

Kim, T.Y. et al., "Pyruvate protects against kainate-induced epileptic brain damage in rats," (2007) Experimental Neurology 208:159-167.
Kovac, S. et al., "Energy depletion in seizures: Anaplerosis as a strategy for future therapies," (2013) Neuropharmacology 69:96-104.
Tome, A. et al., Inhibitory action of antioxidants (ascorbic acid or α-tocopherol) on seizures and brain damage induced by pilocarpine in rats, (2010) Arq Neuropsiquiatr 68(3):355-361.
Xavier, S.M. et al., 'Vitamin C antioxidant effects in hippocampus of adult Wistar rats after seizures and status epilepticus induced by pilocarpine, (2007) Neuroscience Letters 420:76-79.
Yamamoto, H., "Protection of α-ketoglutarate, oxaloacetate, succinate, malate, fumarate and citrate against seizures, lipid peroxidation and mitochondrial DNA damage induced by potassium cyanide," (2006) Abstracts/Toxicology Letters 164S:S178.
Yamamoto, H., "TCA Cycle may play a role for protection against epileptic seizures," Meeting Abstract for Experimental Biology Annual Meeting, FASEB Journal, vol. 23 (2 pages).
Yue, W. et al. "Inhibitory effects of succinic acid on chemical kindling and amygdala electrical kindling in rats," (2002) Acta Pharmacologica Sinica, 23(9):847-850.
Search Report for Application No. GB1313052.1 dated Jan. 16, 2014 (7 pages).
International Search Report and Written Opinion for International Patent Application No. PCT/GB2014/052205 dated Oct. 6, 2014 (10 pages).
Gahr, M. et al. "Succinic semialdehyde dehydrogenase deficiency: an inheritable neurometabolic disease" 2013 Fortschr Neurol Psychiatr. 81(3):154-161.
Ait-El-Mkadem, S. et al. "Mutations in MDH2, Encoding a Krebs Cycle Enzyme, Cause Early-Onset Severe Encephalopathy" 2017 Am J Hum Genet. 100(1):151-159.
Prasad, C. et al. "Pyruvate dehydrogenase deficiency and epilepsy" 2011 Brain Dev 33(10):856-865.
Folbergrova, Á, J. & Kunz, W.S. "Mitchondrial dysfunction in epilepsy" 2012 Mitochondrion 12(1):35-40.
Zsurka, G. & Kunz, W.S. "Mitochondrial dysfunction and seizures: the neuronal energy crisis" 2015 14(9):956-966.
Rychikhin, V.M. et al. "Anticonvulsant effect of dicholine succinate on primary generalized epilepsy model in mice" 2013 Eksp Klin Farmakol 76(3):10-12.
Hadera, M.G. et al. "Triheptanoin partially restores levels of tricarboxylic acid cycle intermediates in the mouse pilocarpine model of epilepsy" 2014 J Neurochem 129(1):107-119.
Zang, J. et al. "Protective effect of succinic acid on cerebellar Purkinje cells of neonatal rats with convulsion" 2016 Zhongguo Dang Dai Er Ke Za Zhi 18(1):85-93.
Gandhi, S. et al. Dopamine Induced Neurodegeneration in a PINK1 Model of Parkinson's Disease (2012) PLoS One 7(5):e37564, doi.10.1371/journal.pone.0037564.
Kovac, S. et al. Prolonged seizure activity impairs mitochondrial bioenergetics and induces cell death (2012) J Cell Sci. 125: 1796-1806, doi. 101242/jcs.099176.

\* cited by examiner

*Primary Examiner* — Dennis Heyer
(74) *Attorney, Agent, or Firm* — Quarles & Brady LLP

(57) ABSTRACT

Compositions for use in a method of treatment, particularly for use in a method of treatment of epilepsy or an epilepsy-related disorder, are provided. Uses of the compositions are also described, along with methods for employing the compositions. The described compositions reduce the frequency and severity of epileptic seizures.

18 Claims, 3 Drawing Sheets

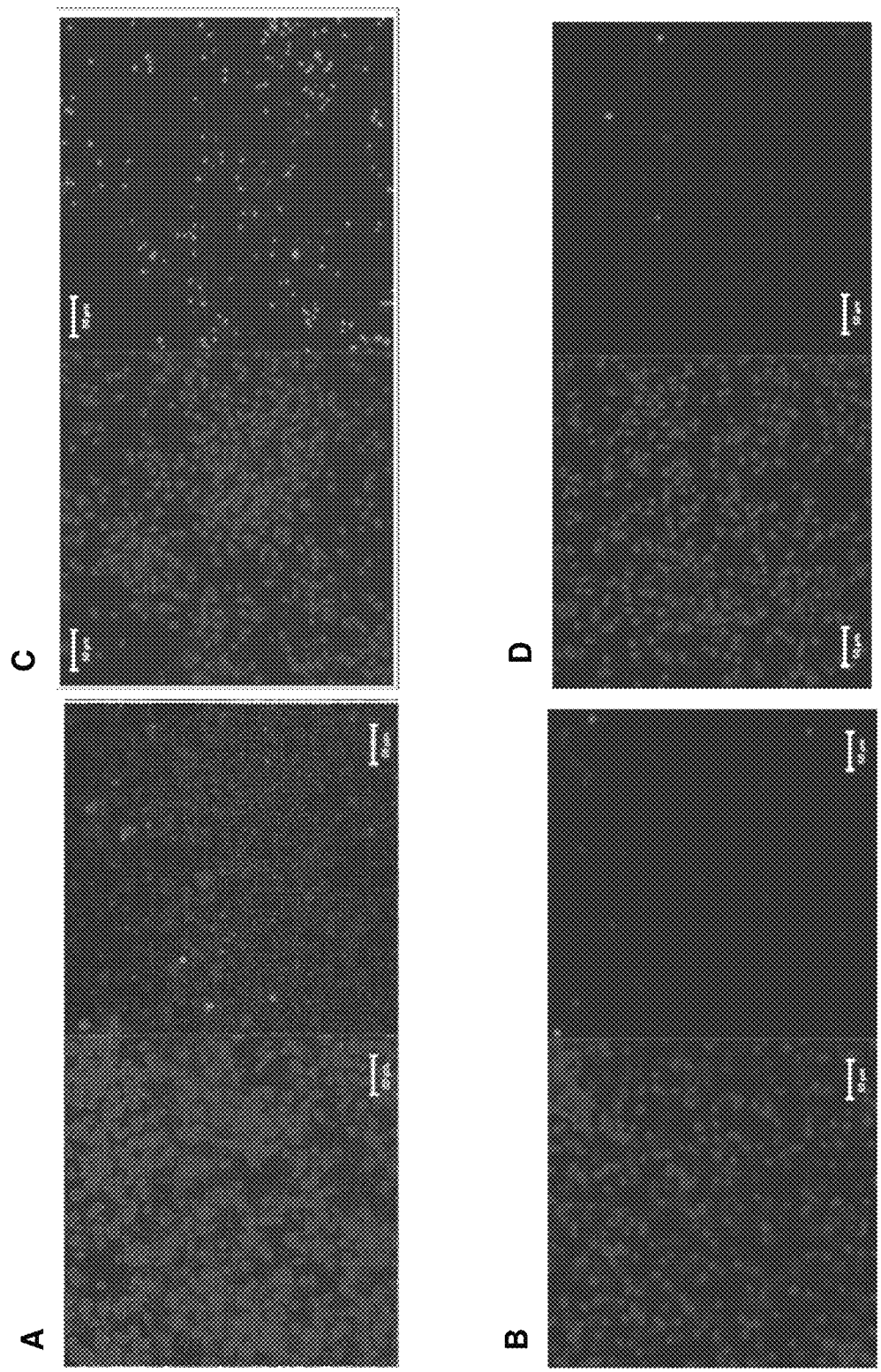
Figure 1. *In-vitro* epilepsy model

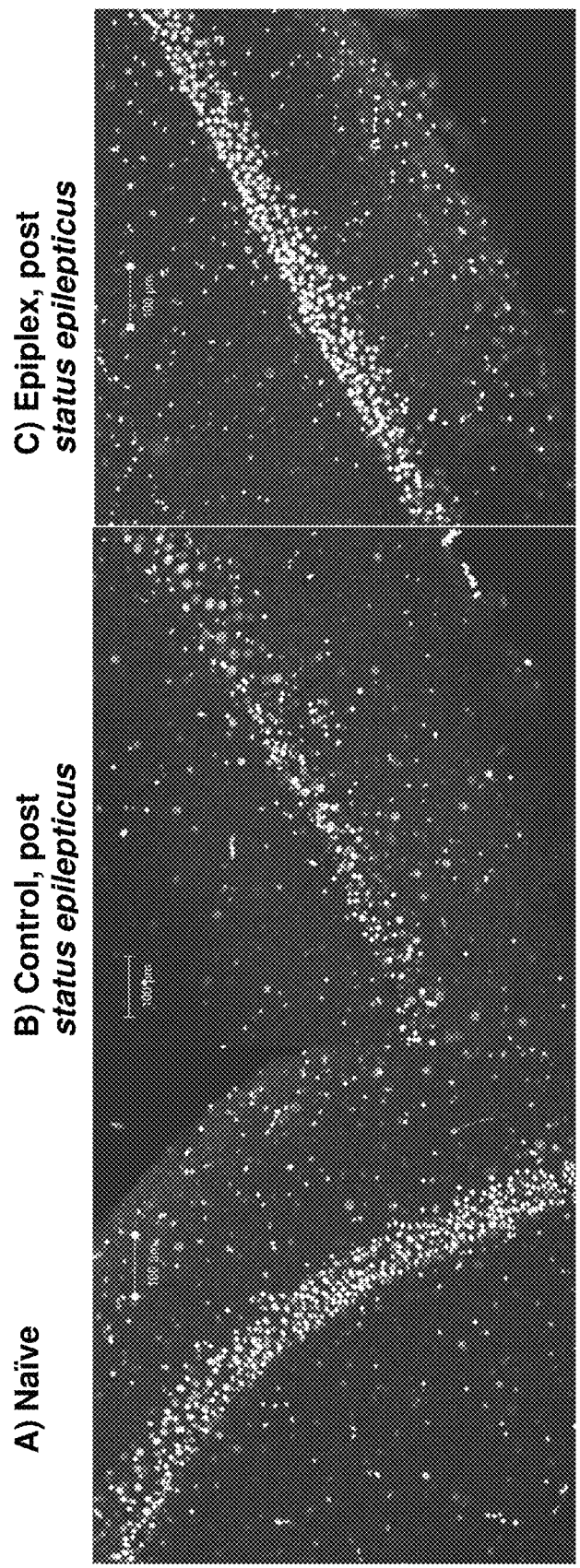
Figure 2. Neuronal density in the CA1 region of the hippocampus

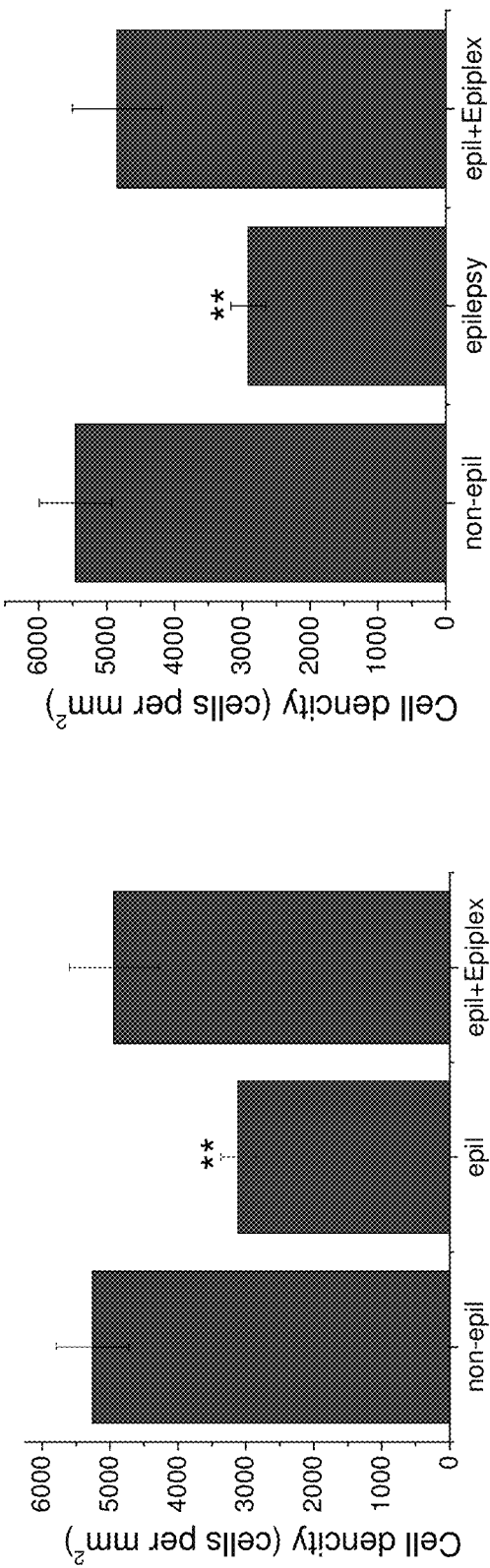
Figure 3. Neuronal density in the CA1 region of the hippocampus

REDUCTION OF EPILEPTIC SEIZURES

CROSS-REFERENCE TO RELATED APPLICATIONS

This patent application is a national stage filing under 35 U.S.C. 371 of international Application No. PCT/GB2014/052205, filed Jul. 18, 2014 which claims the benefit of priority of Great Britain Application No. GB1313052.1, filed Jul. 22, 2013, both of which are incorporated herein by reference in their entireties.

TECHNICAL FIELD

The present invention relates to compositions for reducing the frequency and severity of epileptic seizures, along with uses of those compositions.

BACKGROUND ART

Epilepsy is a common and diverse set of chronic neurological disorders characterized by seizures[1][2]. The diagnosis of epilepsy usually requires that the seizures occur spontaneously. Some definitions of epilepsy require that seizures be recurrent and unprovoked,[1][3][4] but others require only a single seizure combined with brain alterations which increase the chance of future seizures.[5]

Certain epilepsy syndromes require particular precipitants or triggers for seizures to occur. These are termed reflex epilepsy. For example, patients with primary reading epilepsy have seizures triggered by reading.[16] Photosensitive epilepsy can be limited to seizures triggered by flashing lights. Other precipitants can trigger an epileptic seizure in patients who otherwise would be susceptible to spontaneous seizures. For example, children with childhood absence epilepsy may be susceptible to hyperventilation. In fact, flashing lights and hyperventilation are activating procedures used in clinical EEG to help trigger seizures to aid diagnosis. Finally, other precipitants can facilitate, rather than obligately trigger, seizures in susceptible individuals. Emotional stress, sleep deprivation, sleep itself, heat stress, alcohol and febrile illness are examples of precipitants cited by patients with epilepsy. Notably, the influence of various precipitants varies with the epilepsy syndrome.[17] Likewise, the menstrual cycle in women with epilepsy can influence patterns of seizure recurrence. Catamenial epilepsy is the term denoting seizures linked to the menstrual cycle.[18]. Nonetheless, in many cases a cause cannot be identified; however, factors that are associated include brain trauma, strokes, brain cancer, and drug and alcohol misuse among others.[6]

Epilepsy is usually controlled, but not cured, with medication—ant-epileptic drugs (AEDs). The mainstay of AED treatment is anticonvulsant medications. Often, anticonvulsant medication treatment will be lifelong and can have major effects on quality of life. The choice among anticonvulsants and their effectiveness differs by epilepsy syndrome. Mechanisms, effectiveness for particular epilepsy syndromes, and side-effects differ among the individual anticonvulsant medications.

Currently there are 20 medications approved by the Food and Drug Administration for the use of treatment of epileptic seizures in the US: carbamazepine (Tegretol), clorazepate (Tranxene), clonazepam (Klonopin), ethosuximide (Zarontin), felbamate (Felbatol), fosphenytoin (Cerebyx), gabapentin (Neurontin), lacosamide (Vimpat), lamotrigine (Lamictal), levetiracetam (Keppra), oxcarbazepine (Trileptal), phenobarbital (Luminal), phenytoin (Dilantin), pregabalin (Lyrica), primidone (Mysoline), tiagabine (Gabitril), topiramate (Topamax), valproate semisodium (Depakote), valproic acid (Depakene), and zonisamide (Zonegran). Other medications not yet approved by the FDA include clobazam (Frisium), vigabatrin (Sabril), retigabine, brivaracetam, seletracetam, acetazolamide (Diamox), progesterone, adrenocorticotropic hormone (ACTH, Acthar), various corticotropic steroid hormones (prednisone), and bromide.

Other drugs are commonly used to abort an active seizure or interrupt a seizure flurry; these include diazepam (Valium, Diastat) and lorazepam (Ativan). Drugs used only in the treatment of refractory status epilepticus include paraldehyde (Paral), midazolam (Versed), and pentobarbital (Nembutal).

The goal for individual patients is very few or no seizures and minimal side-effects. Most patients achieve this balance best with monotherapy, the use of a single anticonvulsant medication. Some patients, however, require the use of two or more anticonvulsants, despite the increased risk of side-effects. Despite this, about 20% of patients with epilepsy continue to have breakthrough epileptic seizures despite best anticonvulsant treatment [10][11] and ~88% of patients reported at least side-effect (such as mood changes, sleepiness, or unsteadiness in gait).[51]

If a person's epilepsy cannot be brought under control after adequate trials of two or three (experts vary here) different drugs, that person's epilepsy is generally said to be medically refractory. A study of patients with previously untreated epilepsy demonstrated that 47% achieved control of seizures with the use of their first single drug. 14% became seizure free during treatment with a second or third drug. An additional 3% became seizure-free with the use of two drugs simultaneously.[55] However, more than 30% of people with epilepsy do not have seizure control even with the best available medications.

Accordingly, there is an ongoing need for new treatments to reduce the frequency and severity of seizures in epileptic patients, particularly those who have proved resistant to current AEDs.

DISCLOSURE OF THE INVENTION

The present inventors have found a complex of active compounds that reduces the number of epileptic seizures in recognized in vivo models of epilepsy and, moreover, alleviate the adverse effects of seizures when they occur. A further advantage of the composition of the invention is that it can be formulated using compounds that are already present in the human body as metabolites and/or have been demonstrated to be non-toxic. Thus, the composition of the invention avoids the problems of side-effects experienced with many commonly prescribed anti-epileptic drugs ("AEDs").

The components of the composition of the invention are related to metabolic intermediates of the Citric Acid Cycle (Kreb's cycle) and ascorbate (vitamin C). Without wishing to be bound by theory, the inventors believe that this mixture of metabolites and reducing agent helps to restore cellular energy levels and therefore oppose in advance the detrimental effects of neuronal hyperexcitability.

Composition

Accordingly, one aspect of the present invention relates to a pharmaceutical composition comprising one or more of the following components and a pharmaceutically acceptable carrier, diluent or excipient:

(A) a compound of formula (A-I) or (A-II):

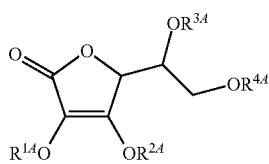
(A-I)

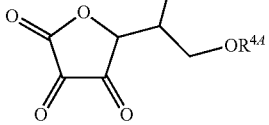
(A-II)

or a tautomer thereof;
or a pharmaceutically acceptable salt, hydrate, or solvate of any of the foregoing;
wherein:
- $R^{1A}$ is independently H or $R^{1AA}$;
- $R^{2A}$ is independently H or $R^{2AA}$;
- $R^{3A}$ is independently H or $R^{3AA}$;
- $R^{4A}$ is independently H or $R^{4AA}$;
- $R^{1AA}$ is independently $R^{1AAA}$ or $C(O)R^{1AAAA}$;
- $R^{2AA}$ is independently $R^{2AAA}$ or $C(O)R^{2AAAA}$;
- $R^{3AA}$ is independently $R^{3AAA}$ or $C(O)R^{3AAAA}$;
- $R^{4AA}$ is independently $R^{3AAA}$ or $C(O)R^{4AAAA}$;
- $R^{1AAA}$ is a linear or branched saturated $C_{1-6}$ alkyl group;
- $R^{2AAA}$ is a linear or branched saturated $C_{1-6}$ alkyl group;
- $R^{3AAA}$ is a linear or branched saturated $C_{1-6}$ alkyl group;
- $R^{4AAA}$ is a linear or branched saturated $C_{1-6}$ alkyl group;
- $R^{1AAAA}$ is a linear or branched saturated $C_{1-6}$ alkyl group;
- $R^{2AAAA}$ is a linear or branched saturated $C_{1-6}$ alkyl group;
- $R^{3AAAA}$ is a linear or branched saturated $C_{7-20}$ alkyl group, or a linear or branched $C_{7-20}$ alkenyl group having 1 to 3 carbon-carbon double bonds; and
- $R^{4AAAA}$ is a linear or branched saturated $C_{7-20}$ alkyl group, or a linear or branched $C_{7-20}$ alkenyl group having 1 to 3 carbon-carbon double bonds;

(B) a compound of formula (B-I):

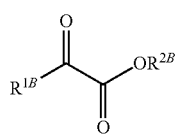
(B-I)

or a pharmaceutically acceptable salt, hydrate, or solvate thereof;
wherein:
$R^{1B}$ is a linear or branched saturated $C_{1-6}$ alkyl group;
$R^{2B}$ is independently H or $R^{2BB}$; and
$R^{2BB}$ is a linear or branched saturated $C_{1-6}$ alkyl group;

(C) a compound of formula (C-I):

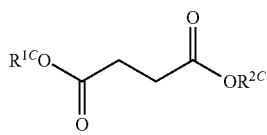
(C-I)

or a pharmaceutically acceptable salt, hydrate, or solvate thereof;
wherein:
- $R^{1C}$ is independently H or $R^{1CC}$;
- $R^{2C}$ is independently H or $R^{2CC}$;
- $R^{1CC}$ is a linear or branched saturated $C_{1-6}$ alkyl group;
- $R^{2CC}$ is a linear or branched saturated $C_{1-6}$ alkyl group; and and
(D) a compound of formula (D-I):

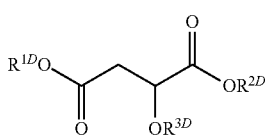
(D-I)

or a pharmaceutically acceptable salt, hydrate, or solvate thereof;
wherein:
- $R^{1D}$ is independently H or $R^{1DD}$;
- $R^{2D}$ is independently H or $R^{2DD}$;
- $R^{3D}$ is independently H or $R^{3DD}$;
- $R^{1DD}$ is a linear or branched saturated $C_{1-6}$ alkyl group;
- $R^{2DD}$ is a linear or branched saturated $C_{1-6}$ alkyl group; and
- $R^{3DD}$ is a linear or branched saturated $C_{1-6}$ alkyl group.

In one embodiment, the pharmaceutical composition comprises component (A) and a pharmaceutically acceptable carrier, diluent or excipient.

In one embodiment, the pharmaceutical composition comprises component (B) and a pharmaceutically acceptable carrier, diluent or excipient.

In one embodiment, the pharmaceutical composition comprises component (C) and a pharmaceutically acceptable carrier, diluent or excipient.

In one embodiment, the pharmaceutical composition comprises component (D) and a pharmaceutically acceptable carrier, diluent or excipient.

In one embodiment, the pharmaceutical composition consists essentially of component (A) and a pharmaceutically acceptable carrier, diluent or excipient.

In one embodiment, the pharmaceutical composition consists essentially of component (B) and a pharmaceutically acceptable carrier, diluent or excipient.

In one embodiment, the pharmaceutical composition consists essentially of component (C) and a pharmaceutically acceptable carrier, diluent or excipient.

In one embodiment, the pharmaceutical composition consists essentially of component (D) and a pharmaceutically acceptable carrier, diluent or excipient.

In one embodiment, the pharmaceutical composition comprises components (A) and (B), and a pharmaceutically acceptable carrier, diluent or excipient.

In one embodiment, the pharmaceutical composition consists essentially of components (A) and (B), and a pharmaceutically acceptable carrier, diluent or excipient.

In one embodiment, the pharmaceutical composition comprises components (A) and (C), and a pharmaceutically acceptable carrier, diluent or excipient.

In one embodiment, the pharmaceutical composition consists essentially of components (A) and (C), and a pharmaceutically acceptable carrier, diluent or excipient.

In one embodiment, the pharmaceutical composition comprises components (A) and (D), and a pharmaceutically acceptable carrier, diluent or excipient.

In one embodiment, the pharmaceutical composition consists essentially of components (A) and (D), and a pharmaceutically acceptable carrier, diluent or excipient.

In one embodiment, the pharmaceutical composition comprises components (B) and (C), and a pharmaceutically acceptable carrier, diluent or excipient.

In one embodiment, the pharmaceutical composition consists essentially of components (B) and (C), and a pharmaceutically acceptable carrier, diluent or excipient.

In one embodiment, the pharmaceutical composition comprises components (B) and (D), and a pharmaceutically acceptable carrier, diluent or excipient.

In one embodiment, the pharmaceutical composition consists essentially of components (B) and (D), and a pharmaceutically acceptable carrier, diluent or excipient.

In one embodiment, the pharmaceutical composition comprises components (C) and (D), and a pharmaceutically acceptable carrier, diluent or excipient.

In one embodiment, the pharmaceutical composition consists essentially of components (C) and (D), and a pharmaceutically acceptable carrier, diluent or excipient.

In one embodiment, the pharmaceutical composition comprises components (A), (B) and (C), and a pharmaceutically acceptable carrier, diluent or excipient.

In one embodiment, the pharmaceutical composition consists essentially of components (A), (B) and (C), and a pharmaceutically acceptable carrier, diluent or excipient.

In one embodiment, the pharmaceutical composition comprises components (A), (B) and (D), and a pharmaceutically acceptable carrier, diluent or excipient.

In one embodiment, the pharmaceutical composition consists essentially of components (A), (B) and (D), and a pharmaceutically acceptable carrier, diluent or excipient.

In one embodiment, the pharmaceutical composition comprises components (A), (C) and (D), and a pharmaceutically acceptable carrier, diluent or excipient.

In one embodiment, the pharmaceutical composition consists essentially of components (A), (C) and (D), and a pharmaceutically acceptable carrier, diluent or excipient.

In one embodiment, the pharmaceutical composition comprises components (B), (C) and (D), and a pharmaceutically acceptable carrier, diluent or excipient.

In one embodiment, the pharmaceutical composition consists essentially of components (B), (C) and (D), and a pharmaceutically acceptable carrier, diluent or excipient.

In one embodiment, the pharmaceutical composition comprises components (A), (B), (C) and (D), and a pharmaceutically acceptable carrier, diluent or excipient.

In one embodiment, the pharmaceutical composition consists essentially of components (A), (B), (C) and (D), and a pharmaceutically acceptable carrier, diluent or excipient.

Component (A)

Component (A) is related to ascorbic acid or dehydroascorbic acid, which have the following structures respectively:

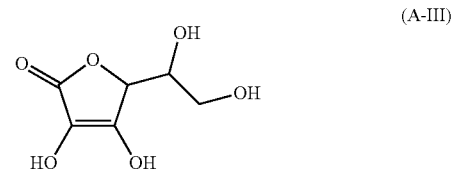

(A-III)

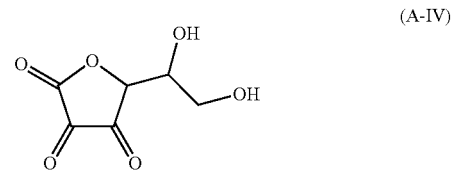

(A-IV)

More specifically, component (A) is a compound of formula (A-I) or (A-II):

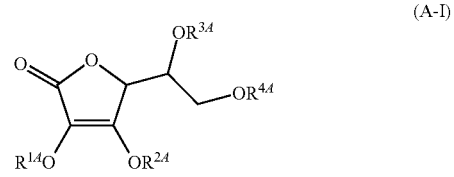

(A-I)

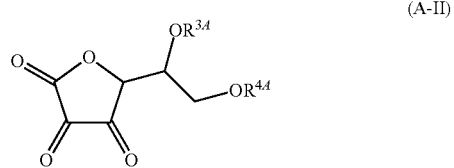

(A-II)

or a tautomer thereof;

or a pharmaceutically acceptable salt, hydrate, or solvate of any of the foregoing;

wherein:
- $R^{1A}$ is independently H or $R^{1AA}$;
- $R^{2A}$ is independently H or $R^{2AA}$;
- $R^{3A}$ is independently H or $R^{3AA}$;
- $R^{4A}$ is independently H or $R^{4AA}$;
- $R^{1AA}$ is independently $R^{1AAA}$ or $C(O)R^{1AAAA}$;
- $R^{2AA}$ is independently $R^{2AAA}$ or $C(O)R^{2AAAA}$;
- $R^{3AA}$ is independently $R^{3AAA}$ or $C(O)R^{3AAAA}$;
- $R^{4AA}$ is independently $R^{3AAA}$ or $C(O)R^{4AAAA}$;
- $R^{1AAA}$ is a linear or branched saturated $C_{1-6}$ alkyl group;
- $R^{2AAA}$ is a linear or branched saturated $C_{1-6}$ alkyl group;
- $R^{3AAA}$ is a linear or branched saturated $C_{1-6}$ alkyl group;
- $R^{4AAA}$ is a linear or branched saturated $C_{1-6}$ alkyl group;
- $R^{1AAAA}$ is a linear or branched saturated $C_{1-6}$ alkyl group;
- $R^{2AAAA}$ is a linear or branched saturated $C_{1-6}$ alkyl group;
- $R^{3AAAA}$ is a linear or branched saturated $C_{7-20}$ alkyl group, or a linear or branched $C_{7-20}$ alkenyl group having 1 to 3 carbon-carbon double bonds; and —R$^{4AAAA}$ is a linear or branched saturated C$_{7-20}$ alkyl group, or a linear or branched C$_{7-20}$ alkenyl group having 1 to 3 carbon-carbon double bonds;

In one embodiment, component (A) is a compound of formula (A-I), or a tautomer thereof, or a pharmaceutically acceptable salt, hydrate, or solvate of any of the foregoing.

In one embodiment, component (A) is a compound of formula (A-II), or a tautomer thereof, or a pharmaceutically acceptable salt, hydrate, or solvate of any of the foregoing.

Note that when R$^{1A}$ and/or R$^{2A}$ of compounds of formula (A-I) are hydrogen, compounds of formula (A-I) may be present in different tautomeric forms. For example, when R$^{1A}$ is hydrogen, compound (A-I) may interconvert between the following tautomers:

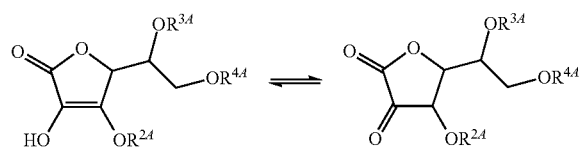

Similarly, when R$^{2A}$ is hydrogen, compounds of formula (A-I) may interconvert between the following tautomers:

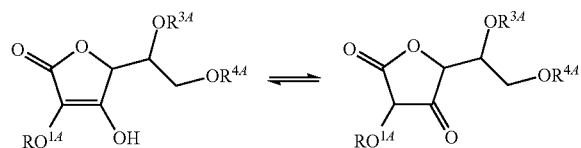

Unless otherwise stated, a reference to one tautomer is intended to be a reference to all tautomers.

Also note that compounds of formula (A-I) and (A-II) have at least two chiral centres, specifically, carbon atoms marked with an asterisk (*) in the following formulae. Each of the carbon atoms at these positions may be in either (R) or (S) configuration. Unless otherwise stated, a reference to one enantiomer/diastereomer is intended to be a reference to both enantiomers/all diastereomers.

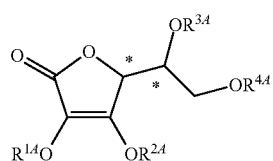
(A-I)

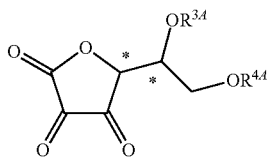
(A-II)

In one embodiment, component (A) is a compound of formula (A-Ia):

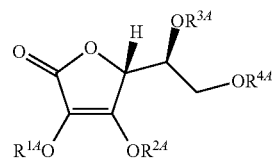
(A-Ia)

or a tautomer thereof;
or a pharmaceutically acceptable salt, hydrate, or solvate of any of the foregoing.

In one embodiment, component (A) is a compound of formula (A-IIa),

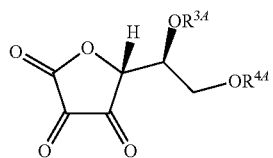
(A-IIa)

or a tautomer thereof;
or a pharmaceutically acceptable salt, hydrate, or solvate of any of the foregoing.

R$^{1A}$
  In one embodiment, R$^{1A}$ is H.
  In one embodiment, R$^{1A}$ is R$^{1AA}$.
R$^{2A}$
  In one embodiment, R$^{2A}$ is H.
  In one embodiment, R$^{2A}$ is R$^{2AA}$.
R$^{3A}$
  In one embodiment, R$^{3A}$ is H.
  In one embodiment, R$^{3A}$ is R$^{3AA}$.
R$^{1AA}$
  In one embodiment, R$^{1AA}$ is R$^{1AAA}$.
  In one embodiment, R$^{1AA}$ is C(O)R$^{1AAAA}$.
R$^{2AA}$
  In one embodiment, R$^{2AA}$ is R$^{2AAA}$.
  In one embodiment, R$^{2AA}$ is C(O)R$^{2AAAA}$.
R$^{3AA}$
  In one embodiment, R$^{3AA}$ is R$^{3AAA}$.
  In one embodiment, R$^{3AA}$ is C(O)R$^{3AAAA}$.
R$^{4AA}$
  In one embodiment, R$^{4AA}$ is R$^{4AAA}$.
  In one embodiment, R$^{4AA}$ is C(O)R$^{4AAAA}$.
R$^{1AAA}$
  In one embodiment, R$^{1AAA}$ is -Me, -Et, -nPr, -iPr, -nBu, -iBu, -sBu, or -tBu.
  In one embodiment, R$^{1AAA}$ is -Me, -Et, -nPr, -iPr.
  In one embodiment, R$^{1AAA}$ is -Me or -Et.
R$^{2AAA}$
  In one embodiment, R$^{2AAA}$ is -Me, -Et, -nPr, -iPr, -nBu, -iBu, -sBu, or -tBu.
  In one embodiment, R$^{2AAA}$ is -Me, -Et, -nPr, -iPr.
  In one embodiment, R$^{2AAA}$ is -Me or -Et.
R$^{3AAA}$
  In one embodiment, R$^{3AAA}$ is -Me, -Et, -nPr, -iPr, -nBu, -iBu, -sBu, or -tBu.
  In one embodiment, R$^{3AAA}$ is -Me, -Et, -nPr, -iPr.
  In one embodiment, R$^{3AAA}$ is -Me or -Et.
R$^{4AAA}$
  In one embodiment, R$^{4AAA}$ is -Me, -Et, -nPr, -iPr, -nBu, -iBu, -sBu, or -tBu.

In one embodiment, $R^{4AAA}$ is -Me, -Et, -nPr, -iPr.
In one embodiment, $R^{4AAA}$ is -Me or -Et.

$R^{1AAAA}$

In one embodiment, $R^{1AAAA}$ is -Me, -Et, -nPr, -iPr, -nBu, -iBu, -sBu, or -tBu.
In one embodiment, $R^{1AAAA}$ is -Me, -Et, -nPr, -iPr.
In one embodiment, $R^{1AAAA}$ is -Me or -Et.

$R^{2AAAA}$

In one embodiment, $R^{2AAAA}$ is -Me, -Et, -nPr, -iPr, -nBu, -iBu, -sBu, or -tBu.
In one embodiment, $R^{2AAAA}$ is -Me, -Et, -nPr, -iPr.
In one embodiment, $R^{2AAAA}$ is -Me or -Et.

$R^{3AAAA}$

In one embodiment, $R^{3AAAA}$ is a linear or branched saturated $C_{7-20}$ alkyl group.
In one embodiment, $R^{3AAAA}$ is a linear saturated $C_{7-20}$ group.
In one embodiment, $R^{3AAAA}$ is a branched saturated $C_{7-20}$ group.
In one embodiment, $R^{3AAAA}$ is a linear or branched saturated $C_{13-20}$ alkyl group.
In one embodiment, $R^{3AAAA}$ is a linear saturated $C_{13-20}$ group.
In one embodiment, $R^{3AAAA}$ is a branched saturated $C_{13-20}$ group.
In one embodiment, $R^{3AAAA}$ is a linear or branched saturated $C_{15-17}$ alkyl group.
In one embodiment, $R^{3AAAA}$ is a linear saturated $C_{15-17}$ group.
In one embodiment, $R^{3AAAA}$ is a branched saturated $C_{15-17}$ group.
In one embodiment, $R^{3AAAA}$ is $C_{15}$ alkyl, such as $C_{15}H_{31}$, for example, a linear $C_{15}H_{31}$ alkyl chain.
In one embodiment, $R^{3AAAA}$ is $C_{17}$ alkyl, such as $C_{17}H_{35}$, for example, a linear $C_{17}H_{35}$ alkyl chain.
In one embodiment $R^{3AAAA}$ is a linear or branched $C_{7-20}$ alkenyl group having 1 to 3 carbon-carbon double bonds.

$R^{4AAAA}$

In one embodiment, $R^{4AAAA}$ is a linear or branched saturated $C_{7-20}$ alkyl group.
In one embodiment, $R^{4AAAA}$ is a linear saturated $C_{7-20}$ group.
In one embodiment, $R^{4AAAA}$ is a branched saturated $C_{7-20}$ group.
In one embodiment, $R^{4AAAA}$ is a linear or branched saturated $C_{13-20}$ alkyl group.
In one embodiment, $R^{4AAAA}$ is a linear saturated $C_{13-20}$ group.
In one embodiment, $R^{4AAAA}$ is a branched saturated $C_{13-20}$ group.
In one embodiment, $R^{4AAAA}$ is a linear or branched saturated $C_{15-17}$ alkyl group.
In one embodiment, $R^{4AAAA}$ is a linear saturated $C_{15-17}$ group.
In one embodiment, $R^{4AAAA}$ is a branched saturated $C_{15-17}$ group.
In one embodiment, $R^{4AAAA}$ is $C_{15}$ alkyl, such as $C_{15}H_{31}$, for example, a linear $C_{15}H_{31}$ alkyl chain.
In one embodiment, $R^{4AAAA}$ is $C_{17}$ alkyl, such as $C_{17}H_{35}$, for example, a linear $C_{17}H_{35}$ alkyl chain.
In one embodiment $R^{4AAAA}$ is a linear or branched $C_{7-20}$ alkenyl group having 1 to 3 carbon-carbon double bonds.

$R^{1A}$, $R^{2A}$, $R^{3A}$, and $R^{4A}$

In a preferred embodiment, component (A) is a compound of formula (A-III):

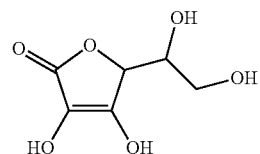

(A-III)

or a tautomer thereof;
or a pharmaceutically acceptable salt, hydrate, or solvate of any of the foregoing.

In one embodiment, component (A) is L-ascorbic acid:

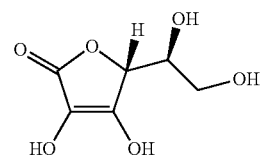

(A-IIIa)

or a tautomer thereof;
or a pharmaceutically acceptable salt, hydrate, or solvate of any of the foregoing.

In another embodiment, component (A) is D-ascorbic acid:

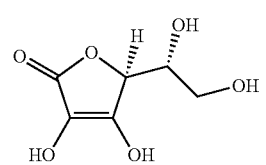

(A-IIIb)

or a tautomer thereof;
or a pharmaceutically acceptable salt, hydrate, or solvate of any of the foregoing.

In another preferred embodiment, component (A) is a compound of formula (A-IV):

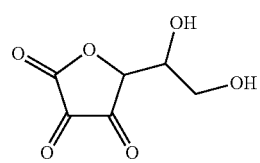

(A-IV)

or a tautomer thereof;
or a pharmaceutically acceptable salt, hydrate, or solvate of any of the foregoing.

In one embodiment, component (A) is L-dehydroascorbic acid:

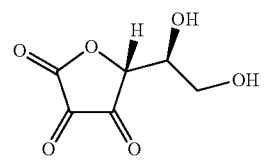

(A-IVa)

or a tautomer thereof;
or a pharmaceutically acceptable salt, hydrate, or solvate of any of the foregoing.

In another embodiment, component (A) is D-dehydroascorbic acid:

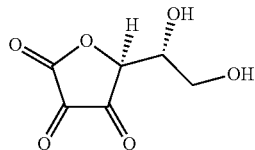

(A-IVb)

or a tautomer thereof;
or a pharmaceutically acceptable salt, hydrate, or solvate of any of the foregoing.

Salts

In one embodiment, component (A) is a pharmaceutically acceptable salt of a compound of formula (A-I), (A-II), (A-Ia), (A-IIb), (A-III), (A-IV), (A-IIIa), (A-IVa), (A-IIIb) or (A-IVb), as discussed below.

Especially suitable pharmaceutically acceptable salts include compounds where $R^{1A}$ is $M^{1A}$ where $M^{1A}$ is a metal cation, for example, a metal cation selected from $Na^+$, $K^+$, $Ca^{2+}$, $Mg^{2+}$, $Cr^{2+}$, $Mn^{2+}$, $Fe^{2+}$, $Zn^{2+}$, and $Mo^{3+}$.

Component (B)

Component (B) is a compound of formula (B-I):

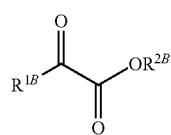

(B-I)

or a pharmaceutically acceptable salt, or a hydrate, or solvate thereof;
wherein:
$R^{1B}$ is a linear or branched saturated $C_{1-6}$ alkyl group;
$R^{2B}$ is independently H or $R^{2BB}$; and
$R^{2BB}$ is a linear or branched saturated $C_{1-6}$ alkyl group.

$R^{1B}$

In one embodiment, $R^{1B}$ is a linear saturated $C_{1-6}$ alkyl group.

In one embodiment, $R^{1B}$ is -Me, -Et, -nPr, -iPr, -nBu, -iBu, -sBu, or -tBu.

In one embodiment, $R^{1B}$ is -Me, -Et, -nPr, -iPr.

In one embodiment, $R^{1B}$ is -Me or -Et.

In one embodiment, $R^{1B}$ is -Me.

$R^{2B}$

In one embodiment, $R^{2B}$ is hydrogen.

In one embodiment, $R^{2B}$ is $R^{2BB}$.

$R^{2BB}$

In one embodiment, $R^{2BB}$ is a linear saturated $C_{1-6}$ alkyl group.

In one embodiment, $R^{2BB}$ is -Me, -Et, -nPr, -iPr, -nBu, -iBu, -sBu, or -tBu.

In one embodiment, $R^{2BB}$ is -Me, -Et, -nPr, -iPr.

In one embodiment, $R^{2BB}$ is -Me or -Et.

In one embodiment, $R^{2BB}$ is -Me.

$R^{1B}$ and $R^{2B}$

In a preferred embodiment, $R^{1B}$ is methyl and $R^{2B}$ is hydrogen; that is, component (B) is pyruvic acid:

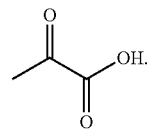

(B-II)

Salts

In one embodiment, component (B) is a pharmaceutically acceptable salt of a compound of formula (B-I) or (B-II), as discussed below.

Especially suitable pharmaceutically acceptable salts include compounds where $R^{2B}$ is $M^{2B}$, where $M^{2B}$ is a pharmaceutically acceptable cation. For example, $R^{2B}$ may be $M^{2B}$ where $M^{2B}$ is an inorganic cation, such as $Na^+$, $K^+$, $Ca^{2+}$, $Mg^{2+}$, or $Al^{3+}$, or an organic cation, such as an ammonium ion (i.e., $NH_4^+$), substituted ammonium ion (e.g., $NH_3R^+$, $NH_2R_2^+$, $NHR_3^+$, $NR_4^+$), or creatine (i.e., 2-[carbamimidoyl(methyl)amino]acetic acid).

In one embodiment, component (B) is a pharmaceutically acceptable salt of pyruvic acid, such as sodium pyruvate, calcium pyruvate, magnesium pyruvate, or creatine pyruvate.

Component (C)

Component (C) is related to succinic acid, which has the following structure:

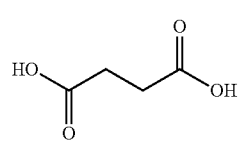

(C-II)

More specifically, component (C) is a compound of formula (C-I):

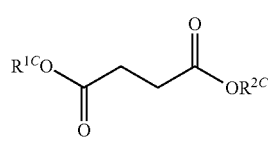

(C-I)

or a pharmaceutically acceptable salt, hydrate, or solvate thereof;
wherein:
—$R^{1C}$ is independently H or $R^{1CC}$;
—$R^{2C}$ is independently H or $R^{2CC}$;
—$R^{1CC}$ is a linear or branched saturated $C_{1-6}$ alkyl group; and
—$R^{2CC}$ is a linear or branched saturated $C_{1-6}$ alkyl group.

$R^{1C}$

In one embodiment, $R^{1C}$ is H.

In one embodiment, $R^{1C}$ is $R^{1CC}$.

$R^{2C}$

In one embodiment, $R^{2C}$ is H.

In one embodiment, $R^{2C}$ is $R^{2CC}$.

$R^{1CC}$

In one embodiment, $R^{1CC}$ is a linear saturated $C_{1-6}$ alkyl group.

In one embodiment, $R^{1CC}$ is -Me, -Et, -nPr, -iPr, -nBu, -iBu, -sBu, or -tBu.

In one embodiment, $R^{1CC}$ is -Me, -Et, -nPr, -iPr.

In one embodiment, $R^{1CC}$ is -Me or -Et.

In one embodiment, $R^{1CC}$ is -Me.

$R^{2CC}$

In one embodiment, $R^{2CC}$ is a linear saturated $C_{1-6}$ alkyl group.

In one embodiment, $R^{2CC}$ is -Me, -Et, -nPr, -iPr, -nBu, -iBu, -sBu, or -tBu.

In one embodiment, $R^{2CC}$ is -Me, -Et, -nPr, -iPr.

In one embodiment, $R^{2CC}$ is -Me or -Et.

In one embodiment, $R^{2CC}$ is -Me.

Salts

In one embodiment, component (C) is a pharmaceutically acceptable salt of a compound of formula (C-I) or (C-II), as described below.

Especially suitable pharmaceutically acceptable salts include compounds where $R^{1C}$ is $M^{1C}$, where $M^{1C}$ is a pharmaceutically acceptable cation. For example, $R^{1C}$ may be $M^{1C}$ where $M^{1C}$ is an inorganic cation, such as $Na^+$, $K^+$, $Ca^{2+}$, $Mg^{2+}$, or $Al^{3+}$, or an organic cation, such as an ammonium ion (i.e., $NH_4^+$), substituted ammonium ion (e.g., $NH_3R^+$, $NH_2R_2^+$, $NHR_3^+$, $NR_4^+$), or creatine (i.e., 2-[carbamimidoyl(methyl)amino]acetic acid).

Especially suitable pharmaceutically acceptable salts include compounds where $R^{2C}$ is $M^{2C}$, where $M^{2C}$ is a pharmaceutically acceptable cation. For example, $R^{2C}$ may be $M^{2C}$ where $M^{2C}$ is an inorganic cation, such as $Na^+$, $K^+$, $Ca^{2+}$, $Mg^{2+}$, or $Al^{3+}$, or an organic cation, such as an ammonium ion (i.e., $NH_4^+$), substituted ammonium ion (e.g., $NH_3R^+$, $NH_2R_2^+$, $NHR_3^+$, $NR_4^+$), or creatine (i.e., 2-[carbamimidoyl(methyl)amino]acetic acid).

Component (D)

Compound (D) is related to malic acid, which has the following structure:

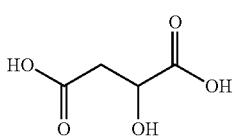

(D-II)

More specifically, component (D) is a compound of formula (D-I):

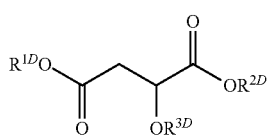

(D-I)

or a pharmaceutically acceptable salt, hydrate, or solvate thereof;
wherein:
—$R^{1D}$ is independently H or $R^{1DD}$;
—$R^{2D}$ is independently H or $R^{2DD}$;
—$R^{3D}$ is independently H or $R^{3DD}$;
—$R^{1DD}$ is a linear or branched saturated $C_{1-6}$ alkyl group;
—$R^{2DD}$ is a linear or branched saturated $C_{1-6}$ alkyl group;

—$R^{3DD}$ is a linear or branched saturated $C_{1-6}$ alkyl group.

Note that the compound of formula (D-I) has at least one chiral centre, specifically, the carbon atom which —$OR^{3D}$ is attached to. The carbon atom at this position may be in either (R) or (S) configuration. Unless otherwise stated, a reference to one enantiomer/diastereomer is intended to be a reference to both enantiomers/all diastereomers.

In one embodiment, component (D) is a compound of formula (D-Ia):

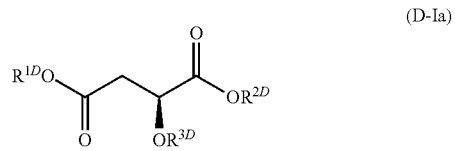

(D-Ia)

In one embodiment, component (D) is a compound of formula (D-Ib):

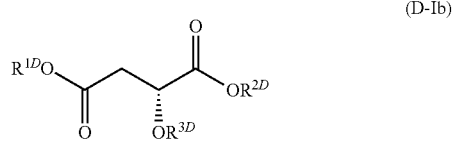

(D-Ib)

$R^{1D}$

In one embodiment, $R^{1D}$ is H.

In one embodiment, $R^{1D}$ is $R^{1DD}$.

$R^{2D}$

In one embodiment, $R^{2D}$ is H.

In one embodiment, $R^{2D}$ is $R^{2DD}$.

$R^{3D}$

In one embodiment, $R^{3D}$ is H.

In one embodiment, $R^{3D}$ is $R^{3DD}$.

$R^{1DD}$

In one embodiment, $R^{1DD}$ is a linear saturated $C_{1-6}$ alkyl group.

In one embodiment, $R^{1DD}$ is -Me, -Et, -nPr, -iPr, -nBu, -iBu, -sBu, or -tBu.

In one embodiment, $R^{1DD}$ is -Me, -Et, -nPr, -iPr.

In one embodiment, $R^{1DD}$ is -Me or -Et.

In one embodiment, $R^{1DD}$ is -Me.

$R^{2DD}$

In one embodiment, $R^{2DD}$ is a linear saturated $C_{1-6}$ alkyl group.

In one embodiment, $R^{2DD}$ is -Me, -Et, -nPr, -iPr, -nBu, -iBu, -sBu, or -tBu.

In one embodiment, $R^{2DD}$ is -Me, -Et, -nPr, -iPr.

In one embodiment, $R^{2DD}$ is -Me or -Et.

In one embodiment, $R^{2DD}$ is -Me.

$R^{3DD}$

In one embodiment, $R^{3DD}$ is a linear saturated $C_{1-6}$ alkyl group.

In one embodiment, $R^{3DD}$ is -Me, -Et, -nPr, -iPr, -nBu, -iBu, -sBu, or -tBu.

In one embodiment, $R^{3DD}$ is -Me, -Et, -nPr, -iPr.

In one embodiment, $R^{3DD}$ is -Me or -Et.

In one embodiment, $R^{3DD}$ is -Me.

Salts

In one embodiment, component (D) is a pharmaceutically acceptable salt of a compound of formula (D-I), (D-Ia), (D-Ib) or (D-II), as described below.

Especially suitable pharmaceutically acceptable salts include compounds where $R^{1D}$ is $M^{1D}$, where $M^{1D}$ is a pharmaceutically acceptable cation. For example, $R^{1D}$ may be $M^{1D}$ where $M^{1D}$ is an inorganic cation, such as $Na^+$, $K^+$, $Ca^{2+}$, $Mg^{2+}$, or $Al^{3+}$, or an organic cation, such as an ammonium ion (i.e., $NH_4^+$), substituted ammonium ion (e.g., $NH_3R^+$, $NH_2R_2^+$, $NHR_3^+$, $NR_4^+$), or creatine (i.e., 2-[carbamimidoyl(methyl)amino]acetic acid).

Especially suitable pharmaceutically acceptable salts include compounds where $R^{2D}$ is $M^{2D}$, where $M^{2D}$ is a pharmaceutically acceptable cation. For example, $R^{2D}$ may be $M^{2D}$ where $M^{2D}$ is an inorganic cation, such as $Na^+$, $K^+$, $Ca^{2+}$, $Mg^{2+}$, or $Al^{3+}$, or an organic cation, such as an ammonium ion (i.e., $NH_4^+$), substituted ammonium ion (e.g., $NH_3R^+$, $NH_2R_2^+$, $NHR_3^+$, $NR_4^+$), or creatine (i.e., 2-[carbamimidoyl(methyl)amino]acetic acid).

Combinations of (A), (B), (C) and (D)

In an especially preferred embodiment, the pharmaceutical composition comprises two or more of the following components and a pharmaceutically acceptable carrier, diluent or excipient:

(A) a compound of formula (A-III) or (A-IV):

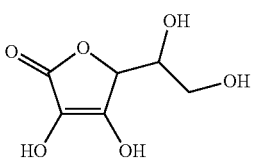
(A-III)

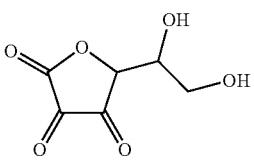
(A-IV)

or a tautomer thereof;
or a pharmaceutically acceptable salt, hydrate, or solvate of any of the foregoing;
(B) a compound of formula (B-II):

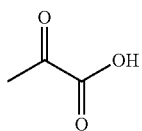
(B-II)

or a pharmaceutically acceptable salt, hydrate, or solvate of any of the foregoing;
(C) a compound of formula (C-II):

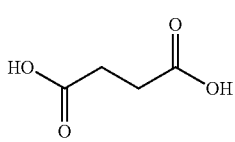
(C-II)

or a pharmaceutically acceptable salt, hydrate, or solvate of any of the foregoing; and (D) a compound of formula (D-II):

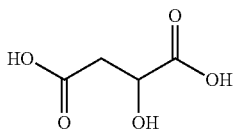
(D-II)

or a pharmaceutically acceptable salt, hydrate, or solvate of any of the foregoing.

Amounts of Components

Suitably, the composition comprises 0.8-1.2 wt. % of component (A), the weight percentage being relative to the total amount of components (A), (B), (C) and (D) in the composition. For example, the composition may comprise 0.9-1.1 wt. % of component (A), such as 0.95-1.05 wt. %.

Suitably, the composition comprises 26-40 wt. % of component (B), the weight percentage being relative to the total amount of components (A), (B), (C) and (D) in the composition. For example, the composition may comprise 28-38 wt. % of component (B), such as 30-36 wt. % or 32-34 wt. %.

Suitably, the composition comprises 26-40 wt. % of component (C), the weight percentage being relative to the total amount of components (A), (B), (C) and (D) in the composition. For example, the composition may comprise 28-38 wt. % of component (C), such as 30-36 wt. % or 32-34 wt. %.

Suitably, the composition comprises 26-40 wt. % of component (D), the weight percentage being relative to the total amount of components (A), (B), (C) and (D) in the composition. For example, the composition may comprise 28-38 wt. % of component (D), such as 30-36 wt. % or 32-34 wt. %.

In one embodiment, the composition comprises 0.8-1.2 wt. % of component (A), 26-40 wt. % of component (B), 26-40 wt. % of component (C), and 26-40 wt. % of component (D), the weight percentages being relative to the total amount of components (A), (B), (C) and (D) in the composition.

In one embodiment, the composition comprises components (A), (B), (C) and (D) at a molar ratio of 2-3:150-230:110-170:100-150 (A:B:C:D).

In one embodiment, the composition comprises components (A), (B), (C) and (D) at a molar ratio of approximately 2:150:110:100 (A:B:C:D).

In one embodiment, the composition comprises 0.8-1.2*wt. % of component (A), 39.5-59.5 wt. % of component (B), and 39.5-59.5 wt. % of component (C), the weight percentages being relative to the total amount of components (A), (B) and (C) in the composition.

In one embodiment, the composition comprises 0.8-1.2 wt. % of component (A), 39.5-59.5 wt. % of component (B), and 39.5-59.5 wt. % of component (D), the weight percentages being relative to the total amount of components (A), (B) and (D) in the composition.

In one embodiment, the composition comprises 0.8-1.2 wt. % of component (A), 39.5-59.5 wt. % of component (C), and 39.5-59.5 wt. % of component (D), the weight percentages being relative to the total amount of components (A), (C) and (D) in the composition.

In one embodiment, the composition comprises 26-40 wt. % of component (B), 26-40 wt. % of component (C), and 26-40 wt. % of component (D), the weight percentages being relative to the total amount of components (B), (C) and (D) in the composition.

In one embodiment, the composition comprises components (A), (B) and (C) at a molar ratio of 2-3:230-340:170-250

In one embodiment, the composition comprises components (A), (B) and (C) at a molar ratio of approximately 2:230:170

In one embodiment, the composition comprises components (A), (B) and (D) at a molar ratio of 2-3:230-340:150-225

In one embodiment, the composition comprises components (A), (B) and (D) at a molar ratio of approximately 2:230:150

In one embodiment, the composition comprises components (A), (C) and (D) at a molar ratio of 2-3:170-250:150-225.

In one embodiment, the composition comprises components (A), (C) and (D) at a molar ratio of approximately 2:170:150.

In one embodiment, the composition comprises components (B), (C) and (D) at a molar ratio of 150-230:110-170:100-150.

In one embodiment, the composition comprises components (B), (C) and (D) at a molar ratio of approximately 150:110:100.

In one embodiment, the composition comprises 0.8-1.2 wt. % of component (A) and 98.8-99.2 wt. % of component (B), the weight percentages being relative to the total amount of components (A) and (B) in the composition.

In one embodiment, the composition comprises 0.8-1.2 wt. % of component (A) and 98.8-99.2 wt. % of component (C), the weight percentages being relative to the total amount of components (A) and (C) in the composition.

In one embodiment, the composition comprises 0.8-1.2 wt. % of component (A) and 98.8-99.2 wt. % of component (D), the weight percentages being relative to the total amount of components (A) and (D) in the composition.

In one embodiment, the composition comprises 40-60 wt. % of component (B) and 40-60 wt. % of component (C), the weight percentages being relative to the total amount of components (B) and (C) in the composition.

In one embodiment, the composition comprises 40-60 wt. % of component (B) and 40-60 wt. % of component (D), the weight percentages being relative to the total amount of components (B) and (D) in the composition.

In one embodiment, the composition comprises 40-60 wt. % of component (C) and 40-60 wt. % of component (D), the weight percentages being relative to the total amount of components (C) and (D) in the composition.

In one embodiment, the composition comprises components (A) and (B) at a molar ratio of 1-1.5:281-282.

In one embodiment, the composition comprises components (A) and (B) at a molar ratio of approximately 1:281.

In one embodiment, the composition comprises components (A) and (C) at a molar ratio of 1-1.5:209-210.

In one embodiment, the composition comprises components (A) and (C) at a molar ratio of approximately 1:209.

In one embodiment, the composition comprises components (A) and (D) at a molar ratio of 1-1.5:184-185.

In one embodiment, the composition comprises components (A) and (D) at a molar ratio of approximately 1:184:

In one embodiment, the composition comprises components (B) and (C) at a molar ratio of 230-340:170-250.

In one embodiment, the composition comprises components (B) and (C) at a molar ratio of approximately 230:170.

In one embodiment, the composition comprises components (B) and (D) at a molar ratio of 230-340:150-225.

In one embodiment, the composition comprises components (B) and (D) at a molar ratio of approximately 230-150.

In one embodiment, the composition comprises components (C) and (D) at a molar ratio of 170-250:150-225.

In one embodiment, the composition comprises components (C) and (D) at a molar ratio of approximately 170:150.

General Chemical Synthesis

Many of the compounds of formulae (A-I), (B-I). (C-I) and (D-I) described herein may be obtained from commercial sources. Other compounds of formulae (A-I), (B-I). (C-I) and (D-I) may be prepared using conventional methods known in the art, or by adapting conventional methods known in the art in conventional ways.

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., $C_{1-6}$alkyl includes n-propyl and iso-propyl; butyl includes n-, iso-, sec-, and tert-butyl). However, reference to a specific group or substitution pattern is not intended to include other structural (or constitutional isomers) which differ with respect to the connections between atoms rather than by positions in space. For example, a reference to a methoxy group, —$OCH_3$, is not to be construed as a reference to its structural isomer, a hydroxymethyl group, —$CH_2OH$. The above exclusion does not pertain to the tautomeric forms described above.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of compounds of formula (A-I), (A-II), (A-Ia), (A-IIb), (A-III), (A-IV), (A-IIIa), (A-IVa), (A-IIIb), (A-IVb), (B-I), (B-II), (C-I), (C-II), (D-I), (D-Ia), (D-Ib) or (D-II), for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Unless otherwise specified, a reference to a particular compound also includes salt forms thereof.

Solvates and Hydrates

It may be convenient or desirable to prepare, purify, and/or handle a corresponding solvate of compounds of formula (A-I), (A-II), (A-Ia), (A-IIb), (A-III), (A-IV), (A-IIIa), (A-IVa), (A-IIIb), (A-IVb), (B-I), (B-II), (C-I), (C-II), (D-I), (D-Ia), (D-Ib) or (D-II), or pharmaceutically acceptable salts thereof. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle compounds of formula (A-I), (A-II), (A-Ia), (A-IIb), (A-III), (A-IV), (A-IIIa), (A-IVa), (A-IIIb), (A-IVb), (B-I), (B-II), (C-I), (C-II), (D-I), (D-Ia), (D-Ib) or (D-II), or pharmaceutically acceptable salts thereof, in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, a carboxylic acid group may be protected as an ester for example, as: a $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

Prodrugs

It may be convenient or desirable to prepare, purify, and/or handle compounds of formula (A-I), (A-II), (A-Ia), (A-IIb), (A-III), (A-IV), (A-IIIa), (A-IVa), (A-IIIb), (A-IVb), (B-I), (B-II), (C-I), (C-II), (D-I), (D-Ia), (D-Ib) or (D-II), or pharmaceutically acceptable salts thereof, in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Formulations

While it is possible for the pharmaceutical composition as described herein to be administered alone, it is preferable to present it as a pharmaceutical formulation, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing two or more of components (A), (B), (C) and (D), as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association components (A), (B), (C) and/or (D) with a carrier which constitutes one or more accessory ingredients. In general, the formulations are prepared by uniformly and intimately bringing into association the two or more components selected from (A), (B), (C) and (D) with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

In one embodiment, the pharmaceutical formulation is a solution of the composition in water. In such an embodiment, the lower limit for the amount of the pharmaceutical composition in the water may be 1 mg/L, 10 mg/L, 30 mg/L, 50 mg/L, 100 mg/L, 500 mg/L, 1 g/L, 2 g/L or 5 g/L. In such an embodiment, the upper limit for the amount of the pharmaceutical composition in the water may be 50 mg/L, 100 mg/L, 500 mg/L, 1 g/L, 2 g/L, 5 g/L or 10 g/L.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The components (A), (B), (C) and/or (D) may be dissolved in, suspended in, or admixed with one or more other pharmaceutically acceptable ingredients. The components (A), (B), (C) and/or (D) may be presented in a liposome or other microparticulate which is designed to target the components (A), (B), (C) and/or (D), for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the components (A), (B), (C) and/or (D) in a flavored basis, usually sucrose and acacia or tragacanth. Pastilles typically comprise the components (A), (B), (C) and/or (D) in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the components (A), (B), (C) and/or (D) in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered components (A), (B), (C) and/or (D) moistened with an inert liquid diluent. The tablets may optionally be coated or scored and may be formulated so as to provide slow or controlled release of the components (A), (B), (C) and/or (D) therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the components (A), (B), (C) and/or (D) and a paraffinic or a water-miscible ointment base.

Creams are typically prepared from the components (A), (B), (C) and/or (D) and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of components (A), (B), (C) and/or (D) through the skin or other affected areas. Examples of such dermal penetration enhancers include dimethylsulfoxide and related analogues.

Emulsions are typically prepared from the components (A), (B), (C) and/or (D) and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the components (A), (B), (C) and/or (D) in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the components (A), (B), (C) and/or (D).

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for ocular administration include eye drops wherein the components (A), (B), (C) and/or (D) are dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the components (A), (B), (C) and/or (D), such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the components (A), (B), (C) and/or (D) are dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the components (A), (B), (C) and/or (D) in the liquid is from about 1 ng/mL to about 10 μg/mL, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the pharmaceutical compositions of the present invention, can vary from patient to patient. Determining the optimal dosage will generally involve the balancing of the level of therapeutic benefit against any risk or deleterious side effects. The selected dosage level will depend on a variety of factors including, but not limited to, the activity of the components of the pharmaceutical composition, the route of administration, the time of administration, the rate of excretion of the components of the pharmaceutical composition, the duration of the treatment, other drugs, compounds, and/or materials used in combination, the severity of the condition, and the species, sex, age, weight, condition, general health, and prior medical history of the patient. The amount of pharmaceutical composition and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the pharmaceutical composition is in the range of about 0.01 mg/kg to about 250 mg/kg of body weight per day or any range therein. Preferably, the range is from about 0.1 to about 100.0 mg/kg of body weight per day or any range therein; more preferably, from about 0.5 mg/kg to about 50 mg/kg, or any range therein; more preferably, from about 1.0 to about 30.0 mg/kg of body weight per day, or any range therein. The composition may be administered on a regimen of 1 to 4 times per day. Where a component is present in the composition as a salt, an ester, a prodrug, or the like, the amount administered is calculated on the basis of the parent compound and so the actual weight to be used is increased proportionately.

Use in Medicine

The pharmaceutical compositions and formulations described herein are useful, for example, in methods of treatment of a disorder (e.g., epilepsy or an epilepsy-related disorder), according to the nature of the drug.

Use in Methods of Therapy

Another aspect of the present invention pertains to a pharmaceutical composition or formulation, as described herein, for use in a method of treatment of the human or animal body by therapy, for example, for use a method of treatment of a disorder (e.g., epilepsy or an epilepsy-related disorder) as described herein.

In one aspect the method of treatment is a method of treatment of epilepsy or an epilepsy-related disorder. In some embodiments the treated human or animal is known to be a pharmacoresistant epilepsy patient. In some embodiments the method comprises the step of determining if the treated human or animal is a pharmacoresistant epilepsy patient.

Use in the Manufacture of Medicaments

Another aspect of the present invention pertains to use of a pharmaceutical composition, as described herein, in the manufacture of a pharmaceutical formulation, as described herein, for the treatment of a disorder (e.g., epilepsy or an epilepsy-related disorder), as described herein.

In one embodiment, the medicament comprises the pharmaceutical composition as described herein.

Methods of Treatment

Another aspect of the present invention pertains to a method of treatment, for example, of a disorder (e.g., epilepsy or an epilepsy-related disorder) as described herein, comprising administering to a patient in need of treatment a therapeutically effective amount of a pharmaceutical composition or formulation, as described herein.

In one aspect the method of treatment is a method of treatment of epilepsy or an epilepsy-related disorder. In some embodiments the treated human or animal is known to be a pharmacoresistant epilepsy patient. In some embodiments the method comprises the step of determining if the treated human or animal is a pharmacoresistant epilepsy patient.

Epilepsy and Related Disorders

As used herein, unless otherwise noted, the terms "epilepsy and related disorders" or "epilepsy or related disorder" shall mean any disorder in which a subject (preferably a human adult, child or infant) experiences one or more seizures and/or tremors. Suitable examples include, but are not limited to, epilepsy (including, but not limited to, localization-related epilepsies, generalized epilepsies, epilepsies with both generalized and local seizures, and the like), seizures associated with Lennox-Gastaut syndrome, seizures as a complication of a disease or condition (such as seizures associated with encephalopathy, phenylketonuria, juvenile Gaucher's disubcutsease, Lundborg's progressive myoclonic epilepsy, stroke, head trauma, stress, hormonal changes, drug use or withdrawal, alcohol use or withdrawal, sleep deprivation, fever, infection, and the like), essential tremor, restless limb syndrome, and the like.

Preferably, the disorder is selected from epilepsy (regardless of type, underlying cause or origin), essential tremor or restless limb syndrome, more preferably, the disorder is epilepsy (regardless of type, underlying cause or origin) or essential tremor.

The term "subject" above refers to an animal, preferably a mammal, most preferably a human adult, child or infant, who has been the object of treatment, observation or experiment.

Seizure

A "seizure" is a massive disruption of electrical communication between neurons in the brain, leading to the temporary release of excessive energy in a synchronized form. Repetitive loss of energy leads to exhaustion and depletion of cellular resources, which cause cell death and taken over the years of disease leads to cognitive decline (dementia).

There are many different classifications of seizure. The main characteristic that distinguishes the different categories of seizures is whether the seizure activity is partial (synonymous with focal) or generalized.

Partial seizures are those in which the seizure activity is restricted to discrete areas of the cerebral cortex. If consciousness is fully preserved during the seizure, the clinical manifestations are considered relatively simple and the seizure is termed a simple-partial seizure. If consciousness is impaired, the seizure is termed a complex-partial seizure. An important additional subgroup comprises those seizures that begin as partial seizures and then spread diffusely throughout the cortex, which are known as partial seizures with secondary generalization.

Generalized seizures involve diffuse regions of the brain simultaneously in a bilaterally symmetric fashion. Absence or petit mal seizures are characterized by sudden, brief lapses of consciousness without loss of postural control. Atypical absence seizures typically include a longer duration in the lapse of consciousness, less abrupt onset and cessation, and more obvious motor signs that may include focal or lateralizing features. Generalized Tonic-clonic or grand mal seizures, the main type of generalized seizures, are characterized by abrupt onset, without warning. The initial phase of the seizure is usually tonic contraction of muscles, impaired respiration, a marked enhancement of sympathetic tone leading to increased heart rate, blood pressure, and pupillary size. After 10-20 s, the tonic phase of the seizure typically evolves into the clonic phase, produced by the superimposition of periods of muscle relaxation on the tonic muscle contraction. The periods of relaxation progressively increase until the end of the ictal phase, which usually lasts no more than 1 min. The postictal phase is characterized by unresponsiveness, muscular flaccidity, and excessive salivation that can cause stridorous breathing and partial airway obstruction. Atonic seizures are characterized by sudden loss of postural muscle tone lasting 1-2 s. Consciousness is briefly impaired, but there is usually no postictal confusion. Myoclonic seizures are characterized by a sudden and brief muscle contraction that may involve one part of the body or the entire body.

Thus, in some embodiments a "seizure" is a partial seizure, such as a simple partial seizure, complex partial seizure, or a partial seizure secondarily generalized. In some embodiments a "seizure" is a generalized or complete seizure, such as an absence seizure, myoclonic seizure, clonic seizure, tonic seizure, tonic-clonic seizure or an atonic seizure.

As seizures are a characteristic aspect of the epilepsy, they can for the purposes of the present invention be considered a symptom of epilepsy, or an "epilepsy related disorder".

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment of cancer includes the prophylaxis of cancer, reducing the incidence of cancer, reducing the cancer of dementia, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The term "prevent," as used herein, refers to prophylactic treatment or treatment that prevents one or more symptoms or conditions of a disease, disorder, or conditions described herein. Preventative treatment can be initiated, for example, prior to ("pre-exposure prophylaxis") or following ("post-exposure prophylaxis") an event that precedes the onset of the disease, disorder, or conditions. Preventive treatment that includes administration of a composition described herein. The doses administered may be varied during the course of preventative treatment.

In some embodiments, the treatment of epilepsy or a related disorder means the reduction in the frequency and/or severity of seizures experienced by an individual. For example, in some embodiments the frequency of seizures in a treated individual (as measured over, for example, one year) may be reduced to less than 80% of the seizure frequency before treatment with the compositions of the invention. In some embodiments the frequency of seizures (as measured over, for example, one year) may be reduced to less than 70%, 60%, 50%, 40%, 30%, 20% or less than 10% of the seizure frequency before treatment with compositions of the invention. The severity of a seizure can be measured, for example, by measuring the level of neuronal death after the seizure; for example, by measuring the level of neuronal death in the CA1 region of the hippocampus either 1 day or 6 days after a seizure.

Thus, in some embodiments the compositions of the invention are used in methods of reducing the frequency of seizures, or for reducing neuronal cell death (for example, reducing neuronal cell death in the CA1 region of the hippocampus).

Combination Therapies

The term "treatment" includes combination treatments and therapies, in which two or more treatments or therapies are combined, for example, sequentially or simultaneously. For example, the pharmaceutical formulations described herein may also be used in combination therapies, e.g., in conjunction with other agents, for example, anti-epileptic drugs (AEDs) or anti-convulsant drugs (used herein, refer to an agent capable of treating, inhibiting or preventing seizure activity or ictogenesis when the agent is administered to a subject or patient). Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

In some embodiments, the pharmaceutical compositions or formulations described herein are given together with one or more anti-convulsant and/or anti-epileptic agent.

The particular combination would be at the discretion of the physician who would select dosages using his common general knowledge and dosing regimens known to a skilled practitioner. The agents (i.e., the pharmaceutical formulation described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the pharmaceutical formulation described here, plus one or more other agents) may be formulated together in a single dosage form, or alternatively, the individual agents may be formulated separately and presented together in the form of a kit, optionally with instructions for their use.

Anti-Convulsant and/or Anti-Epileptic Agent

Suitable examples of anti-convulsant and/or anti-epileptic agents include, but are not limited to:

(a) AMPA antagonists such as AMP-397, E-2007, NS-1209, talampanel, and the like;
(b) Benzodiazepines such as diazepam, lorazepam, clonazepam, clobazam, and the like;
(c) Barbiturates such as phenobarbital, amobarbital, methylphenobarbital, primidone, and the like;
(d) Valproates such as valproic acid, valproate semisodium, valpromide, and the like;
(e) GABA agents such as gabapentin, pregabalin, vigabatrin, losigamone, retigabine, rufinamide, SPD-421 (DP-VPA), T-2000, XP-13512, and the like;
(f) Iminostilbenes such as carbamazepine, oxcarbazepine, and the like;
(g) Hydantoins such as phenytoin sodium, mephenytoin, fosphenytoin sodium, and the like;
(h) NMDA antagonists such as harkoseramide, and the like;
(i) Sodium channel blockers such as BIA-2093, C0-1 02862, lamotrigine, and the like;
j) Succinimides such as methsuximide, ethosuximide, and the like; and
(k) AEDS such as acetazolamide, clomthiazole edisilate, zonisamide, felbamate, topiramate, tiagabine, levetiracetam, briveracetam, GSK-362115, GSK-406725, ICA-69673, CBD cannabis derivative, isovaleramide (NPS-1776), carisbamate, safinamide, seletracetam, soretolide, stiripentol, valrocemide, (2S)-(−)-N-(6-chloro-2,3-dihydro-benzo[1,4]dioxin-2-ylmethyl)-sulfamide, and the like.

Other example AEDs are brivaracetam, carisbamate, carbamazepine, clobazam, clonazepam, ethosuximide, felbamate, gabapentin, lacosamide, lamotrigine, levetiracetam, oxcarbazepine, phenobarbital, phenytoin, pregabalin, primidone, retigabine, rufinamide, safinamide, seletracetam, talampanel, tiagabine, topiramate, valproate, vigabatrin, zonisamide, (2S)-(−)-N-(6-chloro-2,3-dihydro-benzo[1,4]dioxin-2-ylmethyl)sulfamide, benzodiazepines, barbiturates and sedative hypnotics.

Pharmacoresistant Epilepsy Patient

As used herein, a "pharmacoresistant epilepsy patient" is a patient with epilepsy or an epilepsy-related disorder whose seizures are not treated by either of at least two different anti-epilepsy drugs (for example, either of at least two of the AEDs listed above). In some embodiments pharmacoresistant epilepsy patient's seizures are not treated by any of at least three different anti-epilepsy drugs (for example, any of at least three of the AEDs listed above).

Other Uses

The pharmaceutical compositions and formulations, as described herein, may also be used as cell culture additives.

The pharmaceutical compositions and formulations, as described herein, may also be used as part of an in vitro assay, for example, in order to determine whether a candidate host is likely to benefit from treatment with the pharmaceutical formulation.

The pharmaceutical compositions and formulations, as described herein, may also be used as a standard, for example, in an assay, in order to identify, characterise, and/or evaluate other pharmaceutical formulations.

Kits

Another aspect of the invention pertains to a kit comprising (a) a pharmaceutical composition or formulation, as described herein, preferably provided in a suitable container and/or with suitable packaging; and (b) instructions for use, for example, written instructions on how to administer the pharmaceutical composition or formulation, etc.

If appropriate, the kit may optionally including appropriate reagents (e.g., buffers, solvents) and devices (e.g., tubes, syringes) for assembly and use (e.g., administration).

The written instructions may also include a list of indications for which the active ingredient is a suitable treatment.

Routes of Administration

The pharmaceutical composition or formulation may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomiser or dry powder delivery device); ocular (e.g., by eyedrops); pulmonary (e.g., by inhalation or insufflation therapy using, e.g., an aerosol, e.g., through the mouth or nose); rectal (e.g., by suppository or enema); vaginal (e.g., by pessary); parenteral, for example, by injection (e.g., infusion), including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one preferred embodiment, the pharmaceutical composition or formulation is administered parenterally, for example, by intravenous infusion.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human. Furthermore, the subject/patient may be any of its forms of development, for example, a foetus.

In one preferred embodiment, the subject/patient is a human.

FIGURES

FIG. 1. In-vitro epilepsy model.
(A) Low magnesium with no EPIPLEX pretreatment;
(B) Low magnesium with EPIPLEX pretreatment;
(C) 4-AP with no EPIPLEX pretreatment;
(D) 4-AP with EPIPLEX pretreatment.

In each of the panels A-D, the left-hand portion of the panel shows Hoechst florescence (all cells) and the right-hand portion of the panel shows propidium iodide fluorescence (non-viable cells)

FIG. 2. Neuronal density in the CA1 region of the hippocampus following an acute episode of Pilocarpine/lithium induced status epilepticus. Panels show Hoechst staining (neuronal cell nuclei)
(A) Naïve animal;
(B) Control animal, post status epilepticus;
(C) Animal pretreated with Epiplex, post status epilepticus.

FIG. 3. Neuronal density in the CA1 region of the hippocampus following an acute episode of Pilocarpine/lithium induced status epilepticus. A) Cell density 1 day after status epilepticus. B) Cell density 6 days after status epilepticus. Bar labels: "non-epil"=Naïve animal; "epil"=Control animal, post status epilepticus; C) "epil+epiplex"=Animal pretreated with Epiplex, post status epilepticus.

MATERIALS AND METHODS

Cell Viability Assessment

To assess cell death, a culture of primary neurons was stained simultaneously with 20 µM propidium iodide (which is excluded from viable cells but exhibits a red fluorescence in nonviable cells following a loss of membrane integrity) and 4.5 µM Hoechst 33342 (Molecular Probes, Eugene; labels nuclei blue, to count the total number of cells). Each experiment was repeated on at least 3-4 different coverslips from independent cultures. Three to four representative regions per coverslip were photographed and analysed. Statistical analysis was performed on the regions.

Pilocarpine/Lithium Model of Generalized Epilepsy

Injections of lithium/pilocarpine reliably induce status epilepticus in conscious laboratory rats. The status epilepticus is characterized by generalized seizures and is associated with a significant acute mortality, as well as neuronal cell loss in the CA1 region of the hippocampus. The effects of the test compound on the brain neuronal damage produced by seizure activity was evaluated on days 1 and 6 after induction of status epilepticus.

EXAMPLES

Example 1

Epiplex Reduces Calcium Oscillations in an In-Vitro Epilepsy Model

A culture of primary neurons can be utilised as an in-vitro model of epilepsy (see, for example, Buck et al., Sagratella et al., Leite et al.). In this model, cellular behaviour similar to that seen in an epileptic attack is induced by replacing normal incubation medium by an (otherwise identical) 'low magnesium medium'. Immediately on placing the neurons into the low magnesium medium, high amplitude cytosolic calcium oscillations are observed. Similar cytosolic calcium oscillations are observed when 100 µM 4-aminopyridine (4-AP) is applied to cultured neurons.

In order to assess the effect of EPIPLEX on this cellular model of epilepsy, primary neuron cultures were incubated with EPIPLEX (100 µM; 0.8-1.2 wt. % ascorbic acid, 26-40 wt. % of sodium pyruvate, 26-40 wt. % succinate, and 26-40 wt. % of D-Malate. for 20 min prior to exposing the culture to either low magnesium medium or 4-AP.

EPIPLEX was observed to have two significant effects. Firstly, pre-treatment with EPIPLEX significantly reduced the amplitude and frequency of calcium oscillations evoked by either low magnesium or 4-AP. Secondly, pre-treatment with EPIPLEX significantly reduced the level of neuronal cell-death observed following 'seizure, as measured by the number of cells exhibiting propidium iodide fluorescence (see FIG. 1).

Example 2

Epiplex Reduces Acute Mortality and Neuronal-Cell Death in the Lithium/Pilocarpine In Vivo Model of a Convulsive Status Epilepticus In order to assess the effect of EPIPLEX on this in vivo model of epilepsy, two groups of 7 animals were selected for testing. One group had 5 g/L EPIPLEX (0.8-1.2 wt. % ascorbic acid, 26-40 wt. % of sodium pyruvate, 26-40 wt. % succinate, and 26-40 wt. % of D-Malate) added to their drinking water for 24 h prior to lithium/pilocarpine treatment.

EPIPLEX was observed to have two significant effects. Firstly, the EPIPLEX group showed significantly reduced mortality, with all 7 animals surviving an episode of acute status epilepticus. In the control group (i.e. no EPIPLEX) only 3 out of 7 animals survived an episode of acute status epilepticus (significant to p<0.05).

Secondly, in the control group (i.e. no EPIPLEX) an episode of acute status epilepticus resulted in a significant neuronal cell loss in the CA1 region of the hippocampus (cell density reduction by 33% and 38% when assessed 1 and 6 days following SE, respectively; significant to P<0.001), resembling neuronal cell loss observed in human patients with hippocampal sclerosis. In contrast, the group of animals given EPIPLEX prior to the episode of acute status epilepticus showed no significant neuronal cell loss in the CA1 region of the hippocampus. The neuronal densities in the CA1 region of these EPIPLEX animals following acute status epilepticus were not different from those in the hippocampi of naïve animals (P>0.05).

REFERENCES

Buck et al. 1978, "Preliminary report on the magnesium deficient rat as a model of epilepsy", Lab Anim Sci. 1978 December; 28(6):680-5.
Sagratella et al. 1987, "Effects of ketamine and (+)cyclazocine on 4-aminopyridine and 'magnesium free' epileptogenic activity in hippocampal slices of rats", Neuropharmacology. 1987 August; 26(8):1181-4.
Leite J P et al. 1990, "Spontaneous recurrent seizures in rats: an experimental model of partial epilepsy", Neurosci Biobehav Rev. 1990 Winter; 14(4):511-7.
Pereira M B et al. 2007, "Study pharmacologic of the GABAergic and glutamatergic drugs on seizures and status epilepticus induced by pilocarpine in adult Wistar rats", Neuroscience Letters, Volume 419, Issue 3, 4 June, Pages 253-257

The invention claimed is:
1. A method of treating epilepsy comprising administering to a patient in need of treatment a therapeutically effective amount of a pharmaceutical composition comprising components (A), (B), (C), and (D) and a pharmaceutically acceptable carrier, diluent or excipient:

(A) a compound of formula (A-I) or (A-II):

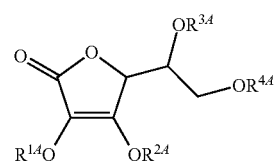

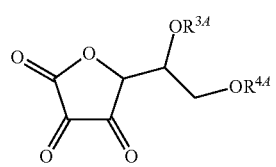

or a tautomer thereof;
or a pharmaceutically acceptable salt, hydrate, or solvate of any of the foregoing;
wherein:
—$R^{1A}$ is independently H or $R^{1AA}$;
—$R^{2A}$ is independently H or $R^{2AA}$;
—$R^{3A}$ is independently H or $R^{3AA}$;
—$R^{4A}$ is independently H or $R^{4AA}$;
—$R^{1AA}$ is independently $R^{1AAA}$ or $C(C)R^{1AAAA}$;
—$R^{2AA}$ is independently $R^{2AAA}$ or $C(O)R^{2AAAA}$;
—$R^{3AA}$ is independently $R^{3AAA}$ or $C(O)R^{3AAAA}$;
—$R^{4AA}$ is independently $R^{3AAA}$ or $C(O)R^{4AAAA}$;
—$R^{1AAA}$ is a linear or branched saturated $C_{1-6}$ alkyl group;
—$R^{2AAA}$ is a linear or branched saturated $C_{1-6}$ alkyl group;
—$R^{3AAA}$ is a linear or branched saturated $C_{1-6}$ alkyl group;
—$R^{4AAA}$ is a linear or branched saturated $C_{1-6}$ alkyl group;
—$R^{1AAAA}$ is a linear or branched saturated $C_{1-6}$ alkyl group;
—$R^{2AAAA}$ is a linear or branched saturated $C_{1-6}$ alkyl group;
—$R^{3AAAA}$ is a linear or branched saturated $C_{7-20}$ alkyl group, or a linear or branched $C_{7-20}$ alkenyl group having 1 to 3 carbon-carbon double bonds; and
—$R^{4AAAA}$ is a linear or branched saturated $C_{7-20}$ alkyl group, or a linear or branched $C_{7-20}$ alkenyl group having 1 to 3 carbon-carbon double bonds;

(B) a compound of formula (B-I):

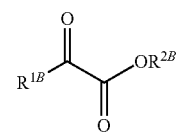

or a pharmaceutically acceptable salt, hydrate, or solvate thereof;
wherein:
$R^{1B}$ is a linear or branched saturated $C_{1-6}$ alkyl group;
$R^{2B}$ is independently H or $R^{2BB}$; and
$R^{2BB}$ is a linear or branched saturated $C_{1-6}$ alkyl group,
wherein the pharmaceutical composition further comprises one or more of components (A), (C), or (D):

(C) a compound of formula (C-I):

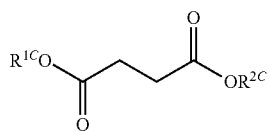
(C-I)

or a pharmaceutically acceptable salt, hydrate, or solvate thereof;
wherein:
—$R^{1C}$ is independently H or $R^{1CC}$;
—$R^{2C}$ is independently H or $R^{2CC}$;
—$R^{1CC}$ is a linear or branched saturated $C_{1-6}$ alkyl group;
—$R^{2CC}$ is a linear or branched saturated $C_{1-6}$ alkyl group;
and
and
(D) a compound of formula (D-I):

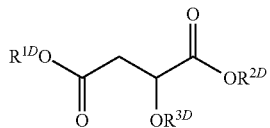
(D-I)

or a pharmaceutically acceptable salt, hydrate, or solvate thereof;
wherein:
—$R^{1D}$ is independently H or $R^{1DD}$;
—$R^{2D}$ is independently H or $R^{2DD}$;
—$R^{3D}$ is independently H or $R^{3DD}$;
—$R^{1DD}$ is a linear or branched saturated $C_{1-6}$ alkyl group;
—$R^{2DD}$ is a linear or branched saturated $C_{1-6}$ alkyl group;
and
—$R^{3DD}$ is a linear or branched saturated $C_{1-6}$ alkyl group.

2. The method of claim 1, wherein the pharmaceutical composition consists of components (A), (B), (C) and (D).

3. The method of claim 1, wherein
(B) is a compound of formula (B-II):

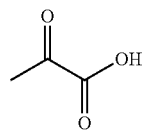
(B-II)

or a pharmaceutically acceptable salt, hydrate, or solvate of any of the foregoing.

4. The method of claim 1, wherein
(A) is a compound of formula (A-III) or (A-IV):

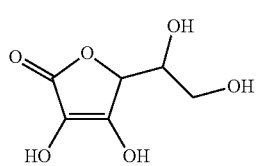
(A-III)

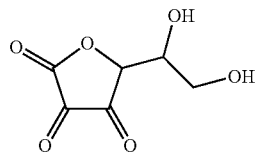
(A-IV)

or a tautomer thereof;
or a pharmaceutically acceptable salt, hydrate, or solvate of any of the foregoing;
(B) is a compound of formula (B-II):

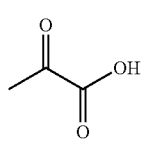
(B-II)

or a pharmaceutically acceptable salt, hydrate, or solvate of any of the foregoing;
(C) is a compound of formula (C-II):

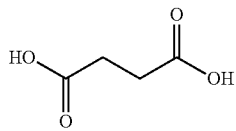
(C-II)

or a pharmaceutically acceptable salt, hydrate, or solvate of any of the foregoing; and
(D) is a compound of formula (D-II):

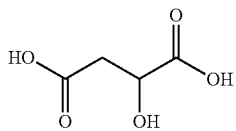
(D-II)

or a pharmaceutically acceptable salt, hydrate, or solvate of any of the foregoing.

5. The method of claim 1, wherein the pharmaceutical composition comprises 0.8-1.2 wt. % of component (A), 26-40 wt. % of component (B), 26-40 wt. % of component (C), and 26-40 wt. % of component (D), the weight percentages being relative to the total amount of components (A), (B), (C) and (D) in the pharmaceutical composition.

6. The method of claim 1, wherein the pharmaceutical composition comprises components (A), (B), (C) and (D) at a molar ratio of 2-3:150-230:110-170:100-150.

7. The method of claim 1, wherein the pharmaceutical composition comprises one or more pharmaceutically acceptable carrier, diluent, excipient, adjuvant, filler, buffer, preservative, anti-oxidant, lubricant, stabiliser, solubiliser, surfactant, masking agent, colouring agent, flavouring agent, sweetening agent, therapeutic agent, or prophylactic agent.

8. The method of claim 1, wherein the pharmaceutical composition comprises water and the concentration of the pharmaceutical composition in water is at least 1 g/L.

9. The method of claim 1, further comprising the step of determining if the treated patient is a pharmacoresistant epilepsy patient.

10. A method of treating epilepsy-related seizures comprising administering to a patient in need of treatment a therapeutically effective amount of a pharmaceutical composition comprising components (A), (B), (C), and (D) and a pharmaceutically acceptable carrier, diluent or excipient:
(A) a compound of formula (A-I) or (A-II):

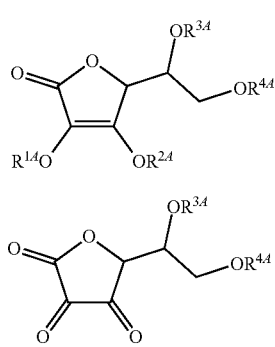

or a tautomer thereof;
or a pharmaceutically acceptable salt, hydrate, or solvate of any of the foregoing;
wherein:
—$R^{1A}$ is independently H or $R^{1AA}$;
—$R^{2A}$ is independently H or $R^{2AA}$;
—$R^{3A}$ is independently H or $R^{3AA}$;
—$R^{4A}$ is independently H or $R^{4AA}$;
—$R^{1AA}$ is independently $R^{1AAA}$ or $C(O)R^{1AAAA}$;
—$R^{2AA}$ is independently $R^{2AAA}$ or $C(O)R^{2AAAA}$;
—$R^{3AA}$ is independently $R^{3AAA}$ or $C(O)R^{3AAAA}$;
—$R^{4AA}$ is independently $R^{3AAA}$ or $C(O)R^{4AAAA}$;
—$R^{1AAA}$ is a linear or branched saturated $C_{1-6}$ alkyl group;
—$R^{2AAA}$ is a linear or branched saturated $C_{1-6}$ alkyl group;
—$R^{3AAA}$ is a linear or branched saturated $C_{1-6}$ alkyl group;
—$R^{4AAA}$ is a linear or branched saturated $C_{1-6}$ alkyl group;
—$R^{1AAAA}$ is a linear or branched saturated $C_{1-6}$ alkyl group;
—$R^{2AAAA}$ is a linear or branched saturated $C_{1-6}$ alkyl group;
—$R^{3AAAA}$ is a linear or branched saturated $C_{7-20}$ alkyl group, or a linear or branched $C_{7-20}$ alkenyl group having 1 to 3 carbon-carbon double bonds; and
—$R^{4AAAA}$ is a linear or branched saturated $C_{7-20}$ alkyl group, or a linear or branched $C_{7-20}$ alkenyl group having 1 to 3 carbon-carbon double bonds;
(B) a compound of formula (B-I):

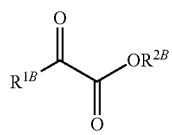

or a pharmaceutically acceptable salt, hydrate, or solvate thereof;
wherein:
$R^{1B}$ is a linear or branched saturated $C_{1-6}$ alkyl group;
$R^{2B}$ is independently H or $R^{2BB}$; and
$R^{2BB}$ is a linear or branched saturated $C_{1-6}$ alkyl group;
wherein the pharmaceutical composition further comprises one or more of components (A), (C), or (D):
(C) a compound of formula (C-I):

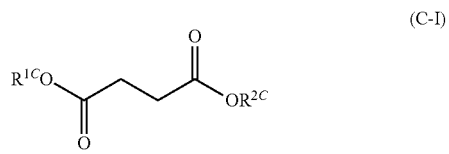

or a pharmaceutically acceptable salt, hydrate, or solvate thereof;
wherein:
—$R^{1C}$ is independently H or $R^{1CC}$;
—$R^{2C}$ is independently H or $R^{2CC}$;
—$R^{1CC}$ is a linear or branched saturated $C_{1-6}$ alkyl group;
—$R^{2CC}$ is a linear or branched saturated $C_{1-6}$ alkyl group;
and
(D) a compound of formula (D-I):

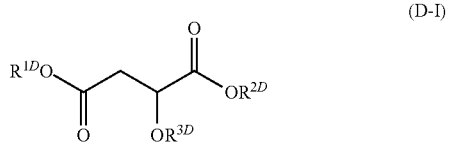

or a pharmaceutically acceptable salt, hydrate, or solvate thereof;
wherein:
—$R^{1D}$ is independently H or $R^{1DD}$;
—$R^{2D}$ is independently H or $R^{2DD}$;
—$R^{3D}$ is independently H or $R^{3DD}$;
—$R^{1DD}$ is a linear or branched saturated $C_{1-6}$ alkyl group;
—$R^{2DD}$ is a linear or branched saturated $C_{1-6}$ alkyl group;
and
—$R^{3DD}$ is a linear or branched saturated $C_{1-6}$ alkyl group.

11. The method of claim 10, wherein the pharmaceutical composition consists of components (A), (B), (C) and (D).

12. The method of claim 10, wherein,
(B) is a compound of formula (B-II):

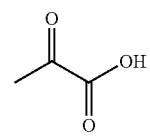

or a pharmaceutically acceptable salt, hydrate, or solvate of any of the foregoing.

13. The method of claim 10, wherein,
(A) is a compound of formula (A-III) or (A-IV):

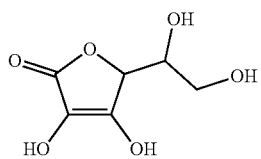

-continued

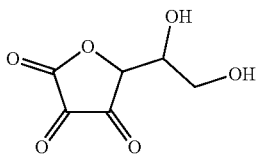
(A-IV)

or a tautomer thereof;
or a pharmaceutically acceptable salt, hydrate, or solvate of any of the foregoing;
(B) is a compound of formula (B-II):

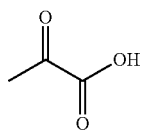
(B-II)

or a pharmaceutically acceptable salt, hydrate, or solvate of any of the foregoing;
(C) is a compound of formula (C-II):

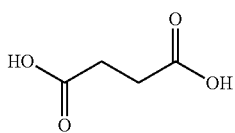
(C-II)

or a pharmaceutically acceptable salt, hydrate, or solvate of any of the foregoing; and (D) is a compound of formula (D-II):

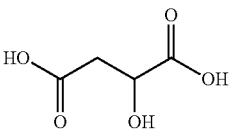
(D-II)

or a pharmaceutically acceptable salt, hydrate, or solvate of any of the foregoing.

14. The method of claim 10, wherein the pharmaceutical composition comprises 0.8-1.2 wt. % of component (A), 26-40 wt. % of component (B), 26-40 wt. % of component (C), and 26-40 wt. % of component (D), the weight percentages being relative to the total amount of components (A), (B), (C) and (D) in the pharmaceutical composition.

15. The method of claim 10, wherein the pharmaceutical composition comprises components (A), (B), (C) and (D) at a molar ratio of 2-3:150-230:110-170:100-150.

16. The method of claim 10, wherein the pharmaceutical composition comprises one or more pharmaceutically acceptable carrier, diluent, excipient, adjuvant, filler, buffer, preservative, anti-oxidant, lubricant, stabiliser, solubiliser, surfactant, masking agent, colouring agent, flavouring agent, sweetening agent, therapeutic agent, or prophylactic agent.

17. The method of claim 10, wherein the pharmaceutical composition comprises water and the concentration of the pharmaceutical composition in water is at least 1 g/L.

18. The method of claim 10, further comprising the step of determining if the treated patient is a pharmacoresistant epilepsy patient.

* * * * *